US012618791B2

(12) United States Patent
Huang et al.

(10) Patent No.: US 12,618,791 B2
(45) Date of Patent: May 5, 2026

(54) SOIL MOISTURE DETECTION DEVICE AND SYSTEM

(71) Applicant: Fujian Tiancheng Baode Intelligent Technology Co., Ltd., Fuzhou (CN)

(72) Inventors: Zhongdong Huang, Fuzhou (CN); Jie Yang, Fuzhou (CN)

(73) Assignee: Fujian Tiancheng Baode Intelligent Technology Co., Ltd., Fuzhou (CN)

( * ) Notice: Subject to any disclaimer, the term of this patent is extended or adjusted under 35 U.S.C. 154(b) by 276 days.

(21) Appl. No.: 18/532,187

(22) Filed: Dec. 7, 2023

(65) Prior Publication Data

US 2025/0130194 A1     Apr. 24, 2025

(30) Foreign Application Priority Data

Oct. 24, 2023    (CN) .......................... 202311382808.6

(51) Int. Cl.
　　*G01N 27/12*　　　(2006.01)
　　*G01N 33/24*　　　(2006.01)
(52) U.S. Cl.
　　CPC ......... *G01N 27/121* (2013.01); *G01N 33/246* (2013.01)
(58) Field of Classification Search
　　CPC . A63B 2209/00; A63B 53/042; A63B 53/047; G01N 27/121; G01N 27/223; G01N 33/24; G01N 33/246
　　See application file for complete search history.

(56) References Cited

U.S. PATENT DOCUMENTS

2004/0083833 A1*　5/2004　Hitt ...................... A01G 25/167
　　　　　　　　　　　　　　　　　　　　　　73/866.5
2011/0043230 A1*　2/2011　Morton ................ G01N 33/246
　　　　　　　　　　　　　　　　　　　　　　324/694
2021/0341407 A1*　11/2021　Burkey ................ G01N 27/223

FOREIGN PATENT DOCUMENTS

CN　　　　106324048 A　*　1/2017　.......... G01N 27/221
CN　　　　216350474 U　　4/2022

* cited by examiner

*Primary Examiner* — Judy Nguyen
*Assistant Examiner* — Adam S Clarke
(74) *Attorney, Agent, or Firm* — Birchwood IP

(57)　　　　ABSTRACT

The present disclosure discloses a soil moisture detection device, a first pole and a second pole are set in soil, a power supply switch circuit is controlled through a main control chip, an external voltage is added to a signal oscillation source, voltage is converted into an oscillation signal by the signal oscillation source, oscillation signal reaches a first pole through a first capacitor and a first inductor. When the soil between the first pole and second pole is completely dry, the two are equivalent to an open circuit, and a waveform detection unit can collect strong oscillation signal corresponding to frequency. When the soil between the first pole and second pole is moist, the oscillation signal is transmitted from the first pole to the second pole through the moist soil, an intensity of the oscillation signal corresponding to the frequency collected by the waveform detection unit changes.

19 Claims, 5 Drawing Sheets

SOIL MOISTURE DETECTION DEVICE AND SYSTEM

CROSS-REFERENCE TO RELATED APPLICATIONS

This application claims priority to Chinese Patent Application No. 202311382808.6, filed on Oct. 24, 2023, which is hereby incorporated by reference in its entirety.

TECHNICAL FIELD

The present disclosure relates to the field of soil moisture detection technologies, and in particular, to a soil moisture detection device and system.

BACKGROUND

The existing soil hygrometers is resistance type, which involves inserting two metal probes into the soil and measuring soil moisture by creating a voltage difference between two electrodes. This involves controlling a small amount of current between the two electrodes and calculating a change in resistance value. By associating the change with soil moisture, the soil moisture can be measured. The principle is that as a moisture content in the soil increases, the number of ions in water correspondingly increases, that is, a loading capacity becomes stronger. By detecting a relative number of loaded ions, the humidity of the soil can be obtained. However, in practice, even if the soil contains same moisture content, the number of ions may not be the same, and an ability of current flowing may also be different. This may result in different soils with the same humidity, and different humidity results can be detected. Therefore, resistance type soil hygrometer has a problem of poor measurement accuracy.

For example, CN216350474U, entitled with soil moisture, conductivity, and temperature monitoring device, the device includes a power module for supplying power to the device; contact electrodes for contacting with soil and detecting moisture and electrical conductivity in the soil; a moisture detection module for detecting soil moisture, which is composed of three stainless steel metal rods and connected to internal circuits. When collecting soil conductivity, a microcontroller sends I2C bus commands through EC-SCL and EC-SDA pins of AD5933 to initiate impedance conversion. After conversion, an impedance value of the equivalent impedance RX is read, and the soil conductivity is calculated. Thus, the measurement of soil moisture is realized. This measurement method has the aforementioned issues.

SUMMARY

Therefore, it is necessary to provide a soil moisture detection device to improve accuracy of soil moisture detection.

To achieve the above objectives, the present disclosure provides a soil moisture detection device, which includes a probe providing with an electrode and contacting soil; a first capacitor, a first inductor, a first resistor, a waveform detection unit, a main control chip, and an oscillation signal source; the electrode includes a first pole and a second pole; an output end of the oscillation signal source is electrically connected to an end of the first resistor, an input end of the waveform detection unit, and the first pole through the first capacitor, the first inductor; the second pole is grounded; and an output end of the waveform detection unit is connected to a voltage detection end of the main control chip.

In an embodiment of the present disclosure, the probe is provided with at least two probes, and the first pole and the second pole are located on two different probes.

In an embodiment of the present disclosure, the probe is provided with at least three probes; the soil moisture detection device further includes a functional unit providing on a probe different from the first pole and the second pole, and a signal output end of the functional unit is connected to a functional detection end of the main control chip; the functional unit is a temperature sensing unit or a pH waveform detection unit.

In an embodiment of the present disclosure, the first pole and the second pole are provided on a same probe.

In an embodiment of the present disclosure, the soil moisture detection device further includes a temperature sensing unit, an output end of the temperature sensing unit is connected to a temperature detection end of the main control chip; or the soil moisture detection device further includes a pH waveform detection unit, which is provided between two poles, and an output end of the pH waveform detection unit is connected to a pH detection end of the main control chip.

In an embodiment of the present disclosure, the soil moisture detection device further includes a switching unit, an input end of the switching unit is connected to the output end of the waveform detection unit, and the other input end of the switching unit is connected to an end of the temperature sensing unit or PH waveform detection unit; an output end of the switching unit is connected to the voltage detection end of the main control chip, and a control end of the switching unit is connected to a control end of the main control chip.

In an embodiment of the present disclosure, the soil moisture detection device further includes a display unit and a wireless transmission unit, the wireless transmission unit is connected to the main control chip and transmits humidity parameters to the display unit through the wireless transmission unit.

In an embodiment of the present disclosure, the output end of the waveform detection unit is connected to the voltage detection end of the main control chip through a second resistor or a follower circuit unit; the oscillation signal source is a crystal oscillator or MCU.

In an embodiment of the present disclosure, the soil moisture detection device further includes a second capacitor; one ends of the first capacitor, the first inductor and the first resistor are respectively connected to an end of the second capacitor; and the other end of the second capacitor is connected to one of the two poles.

A soil detection system is further provided, which includes the soil moisture detection device as described in any of the above embodiments.

Different from existing technologies, the above technical solution provides a first pole and a second pole in the soil that needs to detect humidity. The power supply switch circuit is controlled by the main control chip to close, and an external voltage is added to the signal oscillation source. The signal oscillation source converts voltage into an oscillation signal, and the oscillation signal reaches the first pole through the first capacitor and first inductor. When the soil between the first pole and second pole is completely dry, the two are equivalent to an open circuit, at this time, the waveform detection unit can collect strong oscillation signals corresponding to frequency. When the soil between the first pole and second pole is moist, the oscillation signal is transmitted from the first pole to the second pole through the moist soil. At this time, an intensity of the oscillation signals corresponding to the frequency collected by the waveform detection unit changes. By transmitting the change data to the main control chip, the soil moisture data can be calculated by the main control chip. By using the above detection methods, the accuracy of soil moisture detection can be improved, and the practicality of soil moisture detection devices can be enhanced.

NUMERAL REFERENCE

Figures 1, 2:
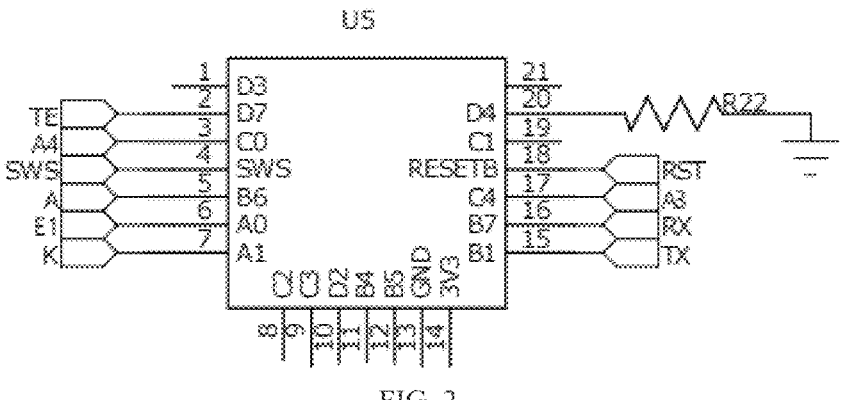
FIG. 1 is a structural schematic diagram of a partial circuit including an oscillation signal source and a waveform detection unit according to a specific implementation mode.
FIG. 2 is a structural schematic diagram of a connection pin of a main control chip according to a specific implementation mode.

1. Soil moisture detection device; 11. First pole; 12. Second pole; 20. Functional unit; 21. Temperature sensing unit; 22. PH waveform detection unit.

DESCRIPTION OF EMBODIMENTS

To provide a detailed explanation of the technical solution, structural features, achieved objectives, and effects of the present disclosure, the following is a detailed explanation combined with specific embodiments and drawings.

Please refer to FIGS. 1 to 8, a soil moisture detection device 10, which includes a probe for providing with two electrodes and contacting with the soil. Its basic structure of the device can refer to existing soil moisture detectors, such as a shell with a circuit board and a main control chip inside the shell. The main control chip is connected to two electrodes through a transmission line, and the electrodes can be fixed on the shell or extended through the transmission line, common electrodes include resistive and capacitive types. The present disclosure improves the resistive soil moisture detection device. Specifically, the soil moisture detection device includes a first pole 11, a second pole 12, a first capacitor (C7), a first inductor (L1), a first resistor (R10), a waveform detection unit, a main control chip (US), and an oscillation signal source (Y1). The first pole 11 and second pole 12 are metal electrodes, in an implementation mode, first pole 11 and second pole 12 are stainless steel, which is not easy to rust and has a long service life. The oscillation signal source can be a crystal oscillator or MCU, and this embodiment uses a crystal oscillator. For example, a quartz crystal oscillator. An output terminal (Y1, 3) of the oscillation signal source is electrically connected to an end of the first resistor, an input end of the waveform detection unit, and the first pole 11 through the first capacitor, the first inductor. The second pole 12 is grounded, and an output terminal of the waveform detection unit is connected to a voltage detection terminal of the main control chip. The first capacitor and the first inductor are connected in series, and a sequence of their series connection is not limited. Specifically, referring to FIG. 1, an output end of the oscillation signal source is connected to an end of the first capacitor, the other end of the first capacitor is connected to an end of the first inductor, the other end of the first inductor is connected to an end of the first resistor, the other end of the first resistor is grounded, and at the same time, the other end of the first inductor is connected to the first pole 11. The waveform detection unit includes a detector (U3) and a detection circuit structure. Specifically, an input end of the detector (U3, 3) is connected to the other end of the first inductor, an output end of the detector (U3, 4) is connected to the voltage detection end of the main control chip, and the detection circuit structure is parallel to the detector and the main control chip. The detection circuit structure specifically includes a third capacitor (C9) and a fourth capacitor (C10), a third resistor (R12) and diode (D2). In an implementation mode, the other end of the first inductor is also connected to an end of a load resistor (R11), and the other end of the load resistor (R11) is connected to the first pole 11 and the input end of the waveform detection unit. By adjusting a resistance value of the load resistor (R11), current value can be adjusted to facilitate a stability testing of the device.

The working principle of this embodiment is as follows: the first pole 11 and the second pole 12 are firstly inserted in the soil where humidity needs to be detected. The power supply switch circuit is controlled by the main control chip to close, and an external voltage is added to the signal oscillation source. The signal oscillation source converts the voltage into an oscillation signal (frequency signal, such as 12/24/50 MHz), and the oscillation signal reaches the first pole 11 through the first capacitor and first inductor. When the soil between the first pole 11 and the second pole 12 is completely dry, the two are equivalent to an open circuit, at this time, the waveform detection unit can collect a strong oscillation signal of a corresponding frequency. When the soil between the first pole 11 and the second pole 12 is moist, the oscillation signal is transmitted from the first pole 11 to the second pole 12 through the moist soil, at this time, an intensity of the oscillation signal of the corresponding frequency collected by the waveform detection unit changes, by transmitting the change data to the main control chip, the soil moisture data can be calculated by the main control chip. By using the above detection methods, the accuracy of soil moisture detection can be improved, and a practicality of the soil moisture detection devices can be enhanced.

The common resistance probe detection devices are single probe or multi probes, and a mechanical structure of the present disclosure can directly apply an existing structure, using an existing mature mechanical structure and processing technology may maintain a low-cost advantage.

Figure 3:
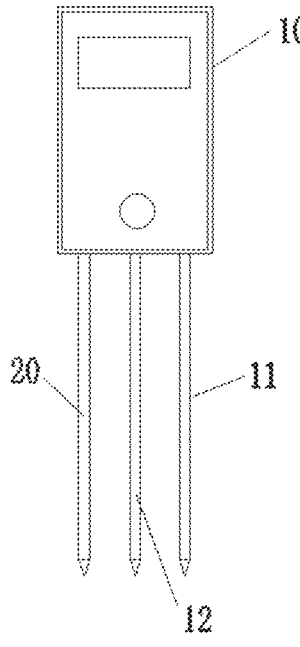
FIG. 3 is a structural schematic diagram of a device with multiple probes according to a specific implementation mode.
Figure 7:
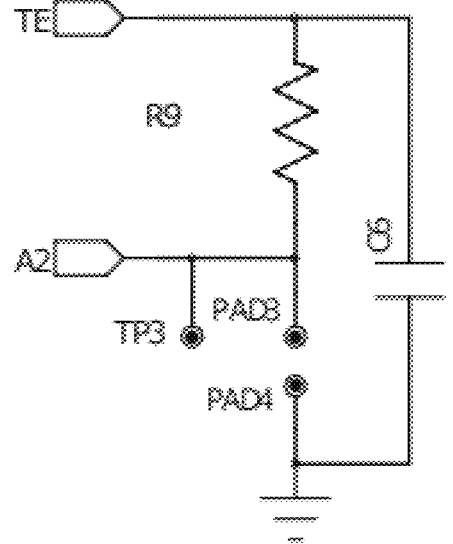
FIG. 7 is a structural schematic diagram of a circuit structure of a functional unit according to a specific implementation mode.

Referring to FIGS. 3 and 7, taking multiple probes as an example, in some embodiments, there are at least two probes, and the first pole 11 and the second pole 12 are located on different probes. By setting the first pole 11 and the second pole 12 on separate probes, an electrical contact between the two can be completely avoided, and a spacing between the two can be adjusted to stably detect soil moisture. However, correspondingly, a production cost of this embodiment is higher than that of a single probe. In an implementation mode, the probe is provided with at least three probes and the soil moisture detection device 10 further includes a functional unit 20, which is set on a probe different from the first pole 11 and the second pole 12, and a signal output terminal (A2) of the functional unit 20 is connected to a functional detection terminal (TE) of the main control chip; the functional unit 20 is a temperature sensing unit 21 or a pH waveform detection unit 22. The temperature sensing unit 21 is a common temperature sensor, such as a soil temperature sensor with a model of HA2002. The pH waveform detection unit 22 can refer to existing probe type soil acidity meters.

Figure 4:
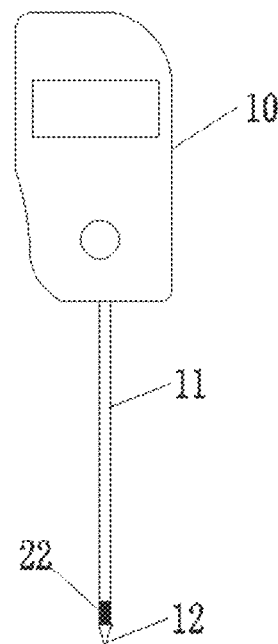
FIG. 4 is a structural schematic diagram of a device with a single probe according to a specific implementation mode.
Figure 5:
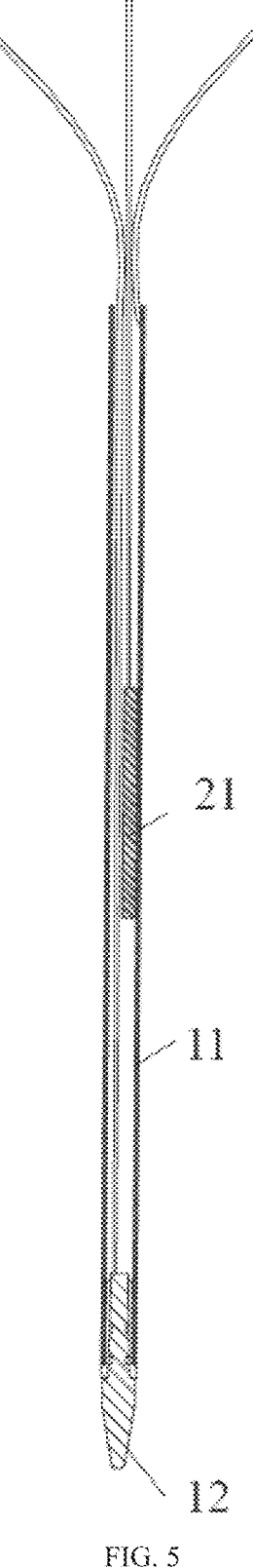
FIG. 5 is a cross-sectional view of the single probe according to a specific implementation mode.
Figure 8:
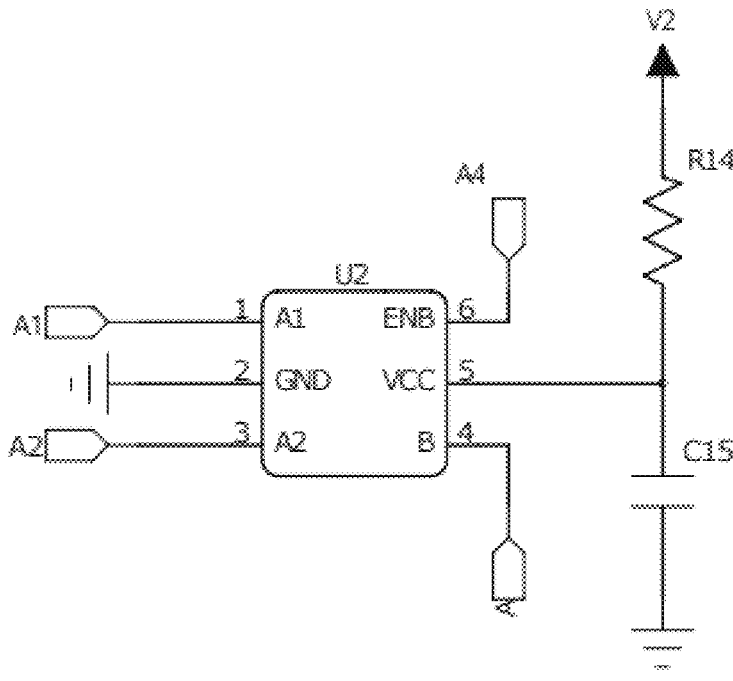
FIG. 8 is a structural schematic diagram of a circuit of a switching unit according to a specific implementation method.

Referring to FIGS. 4-5, in order to reduce costs, in some embodiments, the number of probes is one, that is, a single probe. Specifically, the first pole 11 and the second pole 12 are set on a same probe, as shown in FIG. 5. A probe body of the probe is hollow cylindrical, which can serve as the first pole 11 or the second pole 12, and a corresponding probe head of the probe can serve as the second pole 12 or the first pole 11, a part where the probe head is inserted into the probe body is insulated by injection molding. According to the function of the device, two wires are led out from an inside of the probe body. When the device is equipped with a temperature sensing unit 21 or a pH waveform detection unit 22, four wires can be led out. Two wires are used to connect the two probes, namely the probe body and the probe head, respectively. The other two wires are connected to the temperature sensing unit 21 (thermocouple) or the pH waveform detection unit 22. The temperature sensing unit 21 is located inside the probe, and an output end of the temperature sensing unit 21 is connected to a temperature detection end of the main control chip; the soil moisture detection device 10 further includes a pH waveform detection unit 22, which is set between the two poles, as shown in FIG. 4. A metal absorption section is provided at a front end of the probe to detect pH value. The principle can refer to the existing technology of the probe type soil acidity meter and will not be elaborated here. An output end of the pH waveform detection unit 22 is connected to a pH detection end of the main control chip. Referring to FIG. 8, the soil moisture detection device 10 further includes a switching unit (U2), an input terminal (FIG. 8, A1) of the switching unit is connected to an output terminal of the waveform detection unit (FIG. 1, A1), the other input terminal (FIG. 8, A2) of the switching unit is connected to an end of the temperature sensing unit 21 or the PH waveform detection unit 22 (FIG. 7, A2), and an output terminal of the switching unit (FIG. 8, A) is connected to the voltage detection terminal of the main control chip (FIG. 1, A), a control end (A4) of the switching unit is connected to a control end (FIG. 1, A4) of the main control chip. Due to a possibility of mutual influence when detecting multiple parameters such as humidity, temperature, or pH in a single probe structure, the switching unit can automatically switch the detection function to avoid interference and improve detection accuracy and stability.

In some embodiments, the soil moisture detection device 10 further includes a display unit and a wireless transmission unit, the wireless transmission unit is connected to the main control chip and transmit humidity parameters to the display unit through the wireless transmission unit. The display unit can be a display screen or a projection device. By setting up a display unit at a high altitude or in a control room, humidity data is received through wireless transmission units and displayed on the display unit for easy observation. At the same time, setting the display unit at a position of the soil can also avoid water vapor or salt spray erosion, which can cause display screen failure and thereby prolonging its service life.

Figure 6:
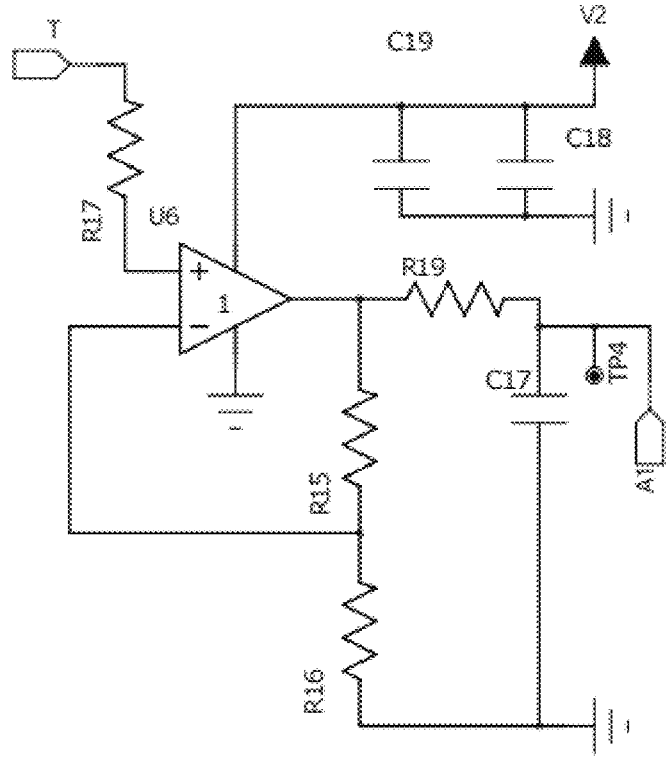
FIG. 6 is a structural schematic diagram of a circuit of a follower circuit unit according to a specific implementation mode.

In some embodiments, referring to FIGS. 1 and 6, an output end of the waveform detection unit is connected to the voltage detection end of the main control chip through a second resistor (R18) or a follower circuit unit. The second resistor is used to adjust current to avoid damaging the circuit due to excessive current. The follower circuit unit plays a role in buffering, isolating, and improving a loading capacity, which can to some extent avoid high output impedance, signal loss generated when an input impedance of the next level is small, ensure that the oscillation signal collected by the waveform detection unit can be stably transmitted to the main control chip, thereby ensuring the stability of humidity detection. The follower circuit unit is consisted by a follower (U6) and a follower circuit structure. The follower, is also known as a buffer amplifier, unit gain amplifier, or isolation amplifier, is an operational amplifier circuit, its output voltage is equal to an input voltage, it only provides buffering, does not amplify the input signal, and the voltage gain is 1.

In some embodiments, the soil moisture detection device 10 further includes a second capacitor (C8), one ends of the first capacitor, first inductor and the first resistor is respectively connected to an end of the second capacitor, where the first capacitor and the first inductor is as a whole, and the other end of the second capacitor is connected to one of the two poles. The second capacitor is used to regulate the oscillation signal emitted by the oscillation signal source, while effectively isolating static electricity from the human body, avoiding a short circuit of the two poles caused by manual operation, which results in excessive instantaneous current in the circuit and damage.

The present disclosure further provides a soil detection system, which is an upper-level integrated system, and includes a data acquisition module, a display module, an information transmission module, and an information storage module. Multiple detection devices can be set in different positions or depths of soil to collect humidity data and transmit it back to the system for calculation and integration. In addition, the system can add corresponding sensors according to detection needs, such as soil conductivity parameters, groundwater level, groundwater quality, air humidity, air temperature, and light intensity.

It should be noted that although the above embodiments have been described in the specification, it does not limit the protection scope of the present disclosure. Therefore, based on the innovative concept of the present disclosure, any changes and modifications made to the embodiments of the present disclosure, or equivalent structural or process transformations made using the description and drawings of the present disclosure, directly or indirectly applying the above technical solutions to other related technical fields, are all within the protection scope of the present disclosure.

What is claimed is:

1. A soil moisture detection device, comprising:
a probe providing with an electrode and contacting soil,
a first capacitor, a first inductor, a first resistor, a waveform detection unit, a main control chip, and an oscillation signal source;
wherein the electrode comprises a first pole and a second pole; an output end of the oscillation signal source is electrically connected to an end of the first resistor, an input end of the waveform detection unit, and the first pole through the first capacitor, the first inductor; the second pole is grounded; and an output end of the waveform detection unit is connected to a voltage detection end of the main control chip;

wherein the soil moisture detection device further comprises a second capacitor; one ends of the first capacitor, the first inductor and the first resistor are respectively connected to an end of the second capacitor; and the other end of the second capacitor is connected to one of the two poles.

2. The soil moisture detection device according to claim 1, wherein the probe is provided with at least two probes, and the first pole and the second pole are located on two different probes.

3. A soil detection system, comprising the soil moisture detection device according to claim 2.

4. The soil moisture detection device according to claim 2, wherein the probe is provided with at least three probes;

the soil moisture detection device further comprises a functional unit providing on a probe different from the first pole and the second pole, and a signal output end of the functional unit is connected to a functional detection end of the main control chip; wherein the functional unit is a temperature sensing unit or a pH waveform detection unit.

5. A soil detection system, comprising the soil moisture detection device according to claim 4.

6. The soil moisture detection device according to claim 4, further comprising a temperature sensing unit, an output end of the temperature sensing unit is connected to a temperature detection end of the main control chip.

7. A soil detection system, comprising the soil moisture detection device according to claim 6.

8. The soil moisture detection device according to claim 6, further comprising a switching unit, wherein an input end of the switching unit is connected to the output end of the waveform detection unit, and the other input end of the switching unit is connected to an end of the temperature sensing unit or PH waveform detection unit; an output end of the switching unit is connected to the voltage detection end of the main control chip, and a control end of the switching unit is connected to a control end of the main control chip.

9. A soil detection system, comprising the soil moisture detection device according to claim 8.

10. The soil moisture detection device according to claim 8, further comprising a switching unit, wherein an input end of the switching unit is connected to the output end of the waveform detection unit, and the other input end of the switching unit is connected to an end of the temperature sensing unit or PH waveform detection unit; an output end of the switching unit is connected to the voltage detection end of the main control chip, and a control end of the switching unit is connected to a control end of the main control chip.

11. A soil detection system, comprising the soil moisture detection device according to claim 10.

12. The soil moisture detection device according to claim 1, wherein the first pole and the second pole are provided on a same probe.

13. A soil detection system, comprising the soil moisture detection device according to claim 12.

14. The soil moisture detection device according to claim 12, further comprising a pH waveform detection unit, which is provided between two poles, and an output end of the pH waveform detection unit is connected to a pH detection end of the main control chip.

15. A soil detection system, comprising the soil moisture detection device according to claim 14.

16. The soil moisture detection device according to claim 1, further comprising a display unit and a wireless transmission unit, wherein the wireless transmission unit is connected to the main control chip and transmits humidity parameters to the display unit through the wireless transmission unit.

17. The soil moisture detection device according to claim 1, wherein the output end of the waveform detection unit is connected to the voltage detection end of the main control chip through a second resistor or a follower circuit unit.

18. The soil moisture detection device according to claim 1, the oscillation signal source is a crystal oscillator or MCU.

19. A soil detection system, comprising the soil moisture detection device according to claim 1.

* * * * *